United States Patent [19]

Stanley et al.

[11] 3,972,918

[45] Aug. 3, 1976

[54] PROCESS FOR SEPARATING DOPA FROM TYROSINE

[75] Inventors: William L. Stanley, El Cerrito; Carl A. Elliger, Berkeley; Bock G. Chan, Albany, all of Calif.

[73] Assignee: The United States of America as represented by the Secretary of Agriculture, Washington, D.C.

[22] Filed: June 28, 1974

[21] Appl. No.: 484,195

[52] U.S. Cl. .............................................. 260/519
[51] Int. Cl.² .......................................... C07C 99/12
[58] Field of Search ...................................... 260/519

[56] References Cited
UNITED STATES PATENTS
3,849,488  11/1974  Brenner .............................. 260/519

*Primary Examiner*—Richard L. Raymond
*Attorney, Agent, or Firm*—M. Howard Silverstein; Max D. Hensley; David G. McConnell

[57] ABSTRACT

Tyrosine and 3,4-dihydroxyphenylalanine (DOPA) are separated from a mixture thereof by applying the mixture to a polymer of p-vinylbenzene boronic acid, and then serially eluting the tyrosine and DOPA.

8 Claims, No Drawings

PROCESS FOR SEPARATING DOPA FROM TYROSINE

DESCRIPTION OF THE INVENTION

This invention relates to and has among its objects the separation of 3,4-dihydroxyphenylalanine (hereinafter referred to as DOPA) from mixtures containing it and tyrosine. Further objects of the invention will be evident from the following description wherein parts and percentages are by weight unless otherwise specified.

L-DOPA is a useful drug in the treatment of Parkinson's disease, an infirmity of the musculatory system. Racemic (or D,L-) DOPA can be synthesized easily and inexpensively. However, separation of L-DOPA, the active component, from the racemic mixture is difficult and consequently expensive.

DOPA can also be prepared from tyrosine by treatment of the latter with the enzyme tyrosine-hydroxylase obtained from red beets. If one starts with L-tyrosine (readily produced from casein), the process wil yield a mixture of L-tyrosine and L-DOPA. The problem, however, is that L-tyrosine and L-DOPA are difficult to separate from one another because of the structural similarities. The two compounds are represented by the following formulae:

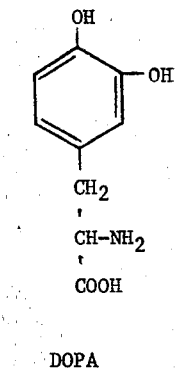

DOPA

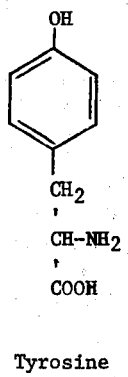

Tyrosine

The invention described herein provides a means for obviating the problems outlined above. By applying the process of the invention, DOPA can be separated from tyrosine rapidly, efficiently, and quantitatively. In addition, the process of the invention can be incorporated with known methods for preparing mixtures of DOPA and tyrosine and the entire procedure can be run continuously.

In the following description attention will be directed to the separation of racemic or DL-DOPA from racemic tyrosine. It should be noted that this direction is by way of illustration only. The invention may be applied with equal success to separate L-DOPA from L-tyrosine or D-DOPA from D-tyrosine. The D and L forms differ, of course, only in the manner in which they rotate plane-polarized light. Other physical and chemical properties are the same.

The process of the invention is based on our finding that when DOPA and tyrosine are applied to a polymer of p-vinylbenzene boronic acid, DOPA is preferentially adsorbed by the polymer. Thus the practice of the invention involves applying a mixture of DOPA and tyrosine to a solid polymer of p-vinylbenzene boronic acid (hereinafter referred to as VBA). The treated polymer is then washed with dilute aqueous alkali to remove the tyrosine while leaving the DOPA adsorbed on the polymer. DOPA is then recovered from the polymer by washing with dilute aqueous acid.

The primary advantage of the invention is that total separation of DOPA from tyrosine is attained. This feature of the invention is important, particularly in the preparation of L-DOPA where purity of the product is essential.

Another advantage of the invention is that it can be adapted to a continuous process. For example, where a mixture of DOPA and tyrosine is prepared by contacting tyrosine with tyrosine hydroxylase, the mixture can be passed through a column containing the polymer. The effluent containing tyrosine, free of DOPA, may be recycled to the enzyme treatment to produce more of the DOPA-tyrosine mixture, which may then be passed through the column.

The recycling mentioned above also provides another advantage. In the enzymatic reaction of tyrosine to produce DOPA, various by-products are produced in small amounts. These impurities deactivate the enzyme, thus "poisoning" it and halting the reaction. If the conversion to DOPA can be maintained at a low level, for example, 2%, the impurity level is so low as to have little detrimental effect on the enzyme. Ordinarily, however, only 2% conversion to DOPA would be impractical. Since the process of the invention can be maintained on a continuous basis in conjunction with the above enzymatic conversion, 2% conversion to DOPA is feasible.

Another advantage of the invention is that the polymer can be used and over. After use in the process of the invention, the resin can be washed with aqueous alkali at about pH 8 whereupon it is ready for reuse. Thus, both time and expense are avoided.

Another advantage of the invention is that it can be applied to separate DOPA from other mixtures containing DOPA. For example, the South American Velvet bean contains approximately 7-8% L-DOPA. The process of the invention is extremely useful in obtaining the L-DOPA from this bean in pure form.

DETAILED DESCRIPTION OF THE INVENTION

The monomer (VBA) employed in the production of the polymers used in the process of the invention is a known compound, having the structure —

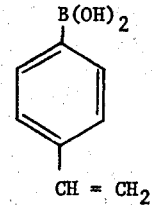

The monomer can be prepared by known methods from p-bromostyrene or p-chlorostyrene as shown by Lennarz et al, J. Amer. Chem. Soc., Vol. 82, pp. 2169–2171, 1960.

For a practice of the invention one may employ homopolymers of VBA or copolymers thereof with styrene or acrylamide. These polymers are prepared by conventional polymerization techniques. For example, VBA per se or admixed with styrene or acrylamide is heated at about 80°–120° C. in a suitable solvent such as diglyme (dimethyl ether of diethylene glycol) containing a small proportion of a polymerization initiator such as α,α'-azobisisobutyronitrile.

The polymers of VBA contain repeating units of the structure —

I.

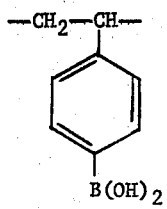

The copolymers of VBA and styrene or acrylamide contain repeating units as in Formula I above plus repeating units of the comonomer, i.e. —

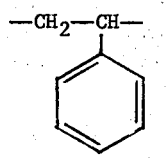

or

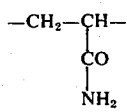

For use in the process of the invention, the resin should be in the granular or bead form. If the resin is in large pieces, grinding is applied to reduce it to granular form. It is also desirable to apply a sieving operation to remove fine particles and oversized particles, retaining those having a mesh size in the range about 40–100 mesh.

In a preferred embodiment, VBA is polymerized on polystyrene beads. This yields a material having excellent properties for use in columns to practice the separation procedure of the invention.

Preferred procedures used in a practice of the invention are described below.

Particles of a solid polymer of VBA are packed into a column, and the mixture of DOPA and tyrosine is applied thereto. The mixture is preferably applied in aqueous solution which is slightly alkaline, i.e., has a pH of about 8–9.

Water buffered to a pH of 8–9 is then passed through the column and the eluate collected, preferably in fractions. Under these alkaline conditions the polymer preferably adsorbs DOPA. Thus, the eluate flowing out of the column will contain only tyrosine. This portion of the eluate can then be collected and the tyrosine recovered by conventional procedures.

After the tyrosine has been thus separated from the mixture, the DOPA may be recovered from the column by either of two alternative procedures.

In the preferred procedures DOPA is recovered by passing dilute aqueous acid through the column to elute it from the polymer. In general, the aqueous acid should have a pH of about 2 to 4 in order to promote facile removal of DOPA from the polymer. The DOPA received in the acidic eluant may be recovered by conventional procedures.

After the acid elution, the column is washed with dilute aqueous alkali of about pH 8 to put the polymer into condition for separating another batch of the mixture of tyrosine and DOPA.

In an alternative procedure to elute DOPA from the column, a large volume of aqueous buffer at pH 8–9 is passed therethrough. This method is less preferred than acid elution because of the large volume of buffer solution required to effect elution of DOPA.

As mentioned above, one particular application of the invention concerns the enzymatic conversion of L-tyrosine to L-DOPA. The conversion is carried out in an aqueous system at a pH of 6–8 and in the presence of tyrosine-hydroxylase. To recover L-DOPA, a portion of the reaction mixture is removed from the time to time, adjusted to pH 8 (where necessary) and applied to a column of VBA polymer. Th eluate containing solely L-tyrosine is collected from the discharge end of the column, and is recycled to the enzymatic reaction system for further conversion to L-DOPA. The column is periodically washed with dilute aqueous acid to recover the L-DOPA. To avoid delay in processing, one may provide two VBA columns so that when one is being regenerated, the other is being used for separation of L-tyrosine and L-DOPA from the enzymatic reaction mixture.

EXAMPLES

The invention is further demonstrated by the following illustrative examples.

Example 1 — Preparation of Styrene-VBA Copolymer

In a 50-ml. flask were placed 5 g. of styrene, 2.5 g. of p-vinylbenzene boronic acid, 5 ml. of diglyme, and 0.1 g. of azobisisobutyronitrile. The flask was purged with argon, sealed, and the contents heated to 80°–90° C. for 1 hour. Heating was continued for an additional hour at 100° C. After cooling, the resulting polymer was removed from the flask and triturated with chloroform in a mortar to reduce the solid polymer to particulate form, which was collected by filtration.

Example 2 — Preparation of VBA Polymer on Polystyrene Beads

A solution of 1 g. of p-vinylbenzene boronic acid in 25 ml. of diglyme containing 0.01 g. of azobisisobutyronitrile was added to 5 g. of porous polysyrene beads (80–100 mesh). The mixture was evacuated to remove entrained air from the polystyrene beads and draw the reaction solution into them. Excess solution was removed with a pipette, and the moist beads were placed in a rotary evaporator where they were heated to about 90° C. for 20 minutes. The beads were then vacuum dried at 120° C. for 1 hour.

To remove unreacted reagents, the dried beads were then treated as follows: The beads were suspended with stirring in 50 ml. of dimethylformamide containing 5% water and warmed to about 80° C. for 1 hour. The beads were collected by filtration, washed successively with methanol and ether, and dried in vacuum. Yield of the VBA-polymer-polystyrene beads was 5.36 g.

Example 3

A column (1 × 21 cm.) was packed with the VBA-polymer-polystyrene beads prepared as in Example 2.

The column was equilibrated by passing 0.1 M potassium phosphate buffer at pH 8 through the column for about 1 hour. A total of 60 ml. of buffer solution was used.

A solution of 20 micromoles each of tyrosine and DOPA was applied to the column which was then eluted with aqueous 0.1 M phosphate buffer at pH 8 at the rate of 60 ml. per hour. The eluate was collected in 5-ml. fractions and analyzed.

It was found that essentially all the tyrosine (20 micromoles) was eluted in the first 20–30 ml. of eluant. An additional 200 ml. of eluate was collected without containing any DOPA.

The eluting liquid was then changed to aqueous 1 M acetic acid at pH 2.5 which was passed through the column at 60 ml. per hour. Essentially all of the DOPA (20 micromoles) was eluted immediately and contained in the first 20–30 ml. of the acid eluate.

Example 4

A solution containing 20 micromoles each of tyrosine and DOPA was applied to a column prepared as in Example 3. The column was eluted at the rate of 60 ml. per hour with aqueous 0.1 M phosphate buffer at pH 8. It was found that tyrosine was collected in the first 20–30 ml. of eluant. DOPA appeared in the eluate only after 250 ml. thereof had passed through the column, and all the DOPA was received in the following 150-ml. portion of the eluate.

Having thus described our invention, we claim:

1. A process for separating DOPA and tyrosine from a mixture of the same, which comprises —
   a. applying the mixture of DOPA and tyrosine to a column containing particles of a solid polymer of p-vinylbenzene boronic acid, said particles having a mesh size in the range about 40–100 mesh, said polymer being a homopolymer containing repeating units of the structure —

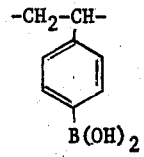

b. eluting the column with buffered aqueous alkali having a pH of about 8 to 9 and collecting the resulting eluate containing solely tyrosine, and
   c. eluting the column with dilute aqueous acid having a pH of about 2 to 4 and collecting the resulting eluate containing soley DOPA.

2. A process for separating DOPA and tyrosine from a mixture of the same, which comprises —
   a. applying the mixture of DOPA and tyrosine to a column containing particles of a solid polymer having a mesh size in the range about 40–100 mesh, said polymer being a copolymer formed from p-vinylbenzene boronic acid and a monomer selected from the group consisting of styrene and acrylamide,
   b. eluting the column with buffered aqueous alkali having a pH of about 8 to 9 and collecting the resulting eluate containing solely tyrosine, and
   c. eluting the column with dilute aqueous acid having a pH of about 2 to 4 and collecting the resulting eluate containing solely DOPA.

3. The process of claim 2 wherein the copolymer is formed from p-vinylbenzene boronic acid and styrene and contains repeating units of the structure —

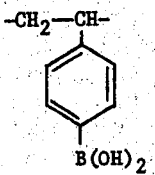

and of the structure —

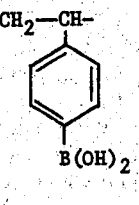

4. The process of claim 2 wherein the copolymer is formed from p-vinylbenzene boronic acid and acrylamide and contains repeating units of the structure —

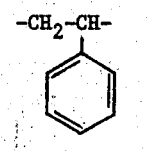

and of the structure -

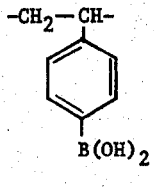

5. A process of separating DOPA and tyrosine from a mixture of the same, which comprises —
   a. applying the mixture to a column containing particles of a solid polymer of p-vinylbenzene boronic acid, said particles having a mesh size in the range about 40–100 mesh, said polymer being a homopolymer containing repeating units of the structure —

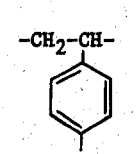

b. eluting the column with buffered aqueous alkali having a pH of about 8 to 9 and collecting the resulting eluate containing solely tyrosine, and
   c. continuing the elution of the column with buffered aqueous alkali having a pH of about 8 to 9 until DOPA appears in the eluate and collecting the subsequent eluant which contains solely DOPA.

6. A process for separating DOPA and tyrosine from a mixture of the same, which comprises —
   a. applying the mixture to a column containing particles of a solid polymer having a mesh size in the range about 40–100 mesh, said polymer being a copolymer formed from p-vinylbenzene boronic acid and a monomer selected from the group consisting of styrene and acrylamide, b. eluting the column with buffered aqueous alkali having a pH of about 8 to 9 and collecting the resulting eluate containing solely tyrosine, and c. continuing the elution of the column with buffered aqueous alkali having a pH of about 8 to 9 until DOPA appears in the eluate and collecting the subsequent eluant which contains solely DOPA.

7. The process of claim 6 wherein the copolymer is formed from p-vinylbenzene boronic acid and styrene and contains repeating units of the structure —

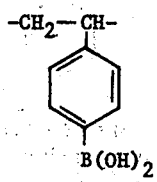

and of the structure —

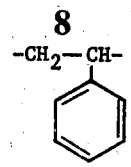

8. The process of claim 6 wherein the copolymer is formed from p-vinylbenzene boronic acid and acrylamide and contains repeating units of the structure —

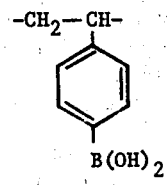

and the structure —

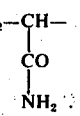

* * * * *